US009858790B1

(12) United States Patent
Goyal et al.

(10) Patent No.: US 9,858,790 B1
(45) Date of Patent: Jan. 2, 2018

(54) INTELLIGENT ALARM CUSTOMIZATION

(71) Applicant: INTERNATIONAL BUSINESS MACHINES CORPORATION, Armonk, NY (US)

(72) Inventors: Munish Goyal, Yorktown Heights, NY (US); Wing L. Leung, Austin, TX (US); Sarbajit K. Rakshit, Kolkata (IN); Kimberly G. Starks, Nashville, TN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/409,796

(22) Filed: Jan. 19, 2017

(51) Int. Cl.
| G08B 23/00 | (2006.01) |
| G08B 21/04 | (2006.01) |
| G10L 25/63 | (2013.01) |
| G06K 9/00 | (2006.01) |

(52) U.S. Cl.
CPC ..... *G08B 21/0423* (2013.01); *G06K 9/00302* (2013.01); *G10L 25/63* (2013.01)

(58) Field of Classification Search
CPC combination set(s) only.
See application file for complete search history.

(56) References Cited

U.S. PATENT DOCUMENTS

| 2008/0079596 | A1* | 4/2008 | Baier ............... G05B 23/0235 340/679 |
| 2011/0015495 | A1 | 1/2011 | Dothie et al. |
| 2012/0300598 | A1* | 11/2012 | Murray ............... G04G 13/02 368/251 |
| 2014/0171146 | A1 | 6/2014 | Ma et al. |
| 2015/0264459 | A1 | 9/2015 | Luna et al. |
| 2015/0363694 | A1* | 12/2015 | Banerjee ............. H04L 67/306 706/46 |
| 2015/0379477 | A1* | 12/2015 | Junqua ............. G06F 17/30292 705/2 |
| 2016/0073951 | A1 | 3/2016 | Kahn et al. |
| 2017/0162197 | A1* | 6/2017 | Cohen ................ G10L 15/22 |

OTHER PUBLICATIONS

"Emotional range", [retrieved on Dec. 7, 2016]. Retrieved from the Internet: <URL: http://www.ibm.com/smarterplanet/us/en/ibmwatson/developercloud/doc/personality-insights/models.shtml#emotionalRange>, 1 pg.

(Continued)

*Primary Examiner* — Travis Hunnings
(74) *Attorney, Agent, or Firm* — Christopher K. McLane; Hye Jin Lucy Song; Heslin Rothenberg Farley & Mesiti PC

(57) ABSTRACT

Methods, computer program products, and systems are presented. The methods include, for instance: collecting user data from the user, analyzing a context of an event including one or more actions from the user data; identifying subsequent actions of the event based on the context of the event, creating one or more context-personality-cognitive state (CPC) mapping and building up a knowledgebase by machine learning, predicting a cognitive state of the user while performing a of the event based on the knowledgebase. The method generates the alarm for the subsequent action based on the predicted first cognitive state of the user and notifying the generated alarm to the user.

20 Claims, 6 Drawing Sheets

(56) References Cited

OTHER PUBLICATIONS

"Understanding the personality models", [retrieved on Dec. 7, 2016]. Retrieved from the Internet: <URL: http://www.ibm.com/smarterplanet/us/en/ibmwatson/developercloud/doc/personality-insights/science.shtml#researchModels>, 1 pg.
Mell, Peter, et al., "The NIST Definition of Cloud Computing", NIST Special Publication 800-145, Sep. 2011, Gaithersburg, MD, 7 pgs.

* cited by examiner

INTELLIGENT ALARM CUSTOMIZATION

TECHNICAL FIELD

The present disclosure relates to personalized alarm automation, and more particularly to methods, computer program products, and systems for intelligently customizing alarm notification according to various cognitive states of users.

BACKGROUND

Conventionally, individual users need to manually set an alarm for each event and to manually adjust the alarm in case of any changes in the scheduled event, regardless of a context and characteristics of the event, and/or varying factors on the users.

SUMMARY

The shortcomings of the prior art are overcome, and additional advantages are provided, through the provision, in one aspect, of a method. The method for customizing an alarm for a user includes, for example: collecting, by one or more processor, user data from the user; analyzing a context of an event from the user data, wherein the event includes one or more actions; identifying subsequent actions of the event based on the context of the event and participants of the event; creating one or more context-personality-cognitive state (CPC) mapping; adding the one or more CPC mapping to a knowledgebase by machine learning; predicting a first cognitive state of the user while performing a first subsequent action amongst the subsequent actions of the event by use of the knowledgebase; and generating the alarm for the first subsequent action based on the predicted first cognitive state of the user and notifying the generated alarm to the user.

Additional features are realized through the techniques set forth herein. Other embodiments and aspects, including but not limited to computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
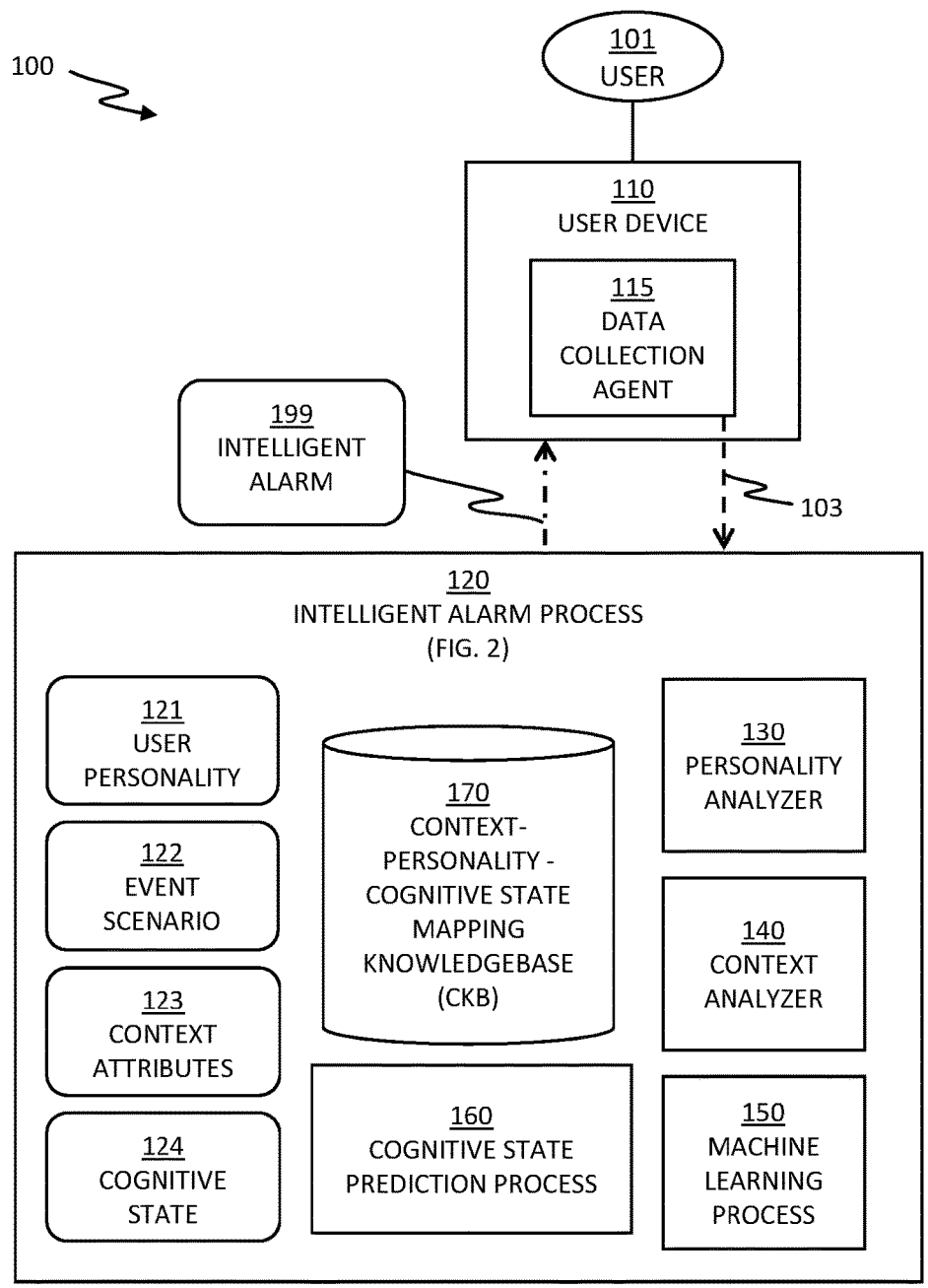
FIG. 1 depicts a system 100 for intelligent personal alarm management, in accordance with one or more embodiments set forth herein.

FIG. 1 depicts a system 100 for intelligent alarm customization, in accordance with one or more embodiments set forth herein.

The system 100 providing intelligent alarm services includes a user 101, a user device 110, and an intelligent alarm process 120. Examples of the user device 110 may be any type of mobile and/or wearable device on the user 101, having various sensors, data capturing, as well as processing capability.

The user device 110 includes a data collection agent 115 running on the user device 110. The data collection agent 115 gathers user data 103 originating from the user 101 and communicates the gathered user data 103 to the intelligent alarm process 120. The data collection agent 115 may be installed in computing environments of the user 101 such as a home network of the user 101 and/or social network servers to which the user 101 subscribes, etc.

The user data 103 are comprehensive information relevant to the user 101 gathered by the data collection agent 115 in real time in order for the intelligent alarm process 120 to identify a personality, behaviors, and cognitive states of the user 101 according to the progression of time. Examples of various user data 103 are presented in FIG. 2 description. The user data 103 may include ambient information related to conditions affecting the user 101, such as a room temperature, various sensor data on a company of the user 101, etc. The data collection agent 115 transmits the user data 103 as gathered on the user device 110 to the intelligent alarm process 120.

The intelligent alarm process 120 automatically sets an intelligent alarm 199 for an event based on the user data 103. The intelligent alarm process 120 includes functional elements of a personality analyzer 130, a context analyzer 140, a machine learning process 150, and a cognitive state prediction process 160. Within the intelligent alarm process 120, the personality analyzer 130 identifies a user personality 121 from the user data 103. The context analyzer 140 generates an event scenario 122 and extracts context attributes 123 of the event by use of the user data 103. Based on the user personality 121, the event scenario 122, and the context attributes 123, the cognitive state prediction process 160 predicts a cognitive state 124. The intelligent alarm process 120 generates one (1) or more context-personality-cognitive state (CPC) mapping by correlating the context attributes 123, the user personality 121, and the cognitive state 124. The intelligent alarm process 120 learns the CPC mapping in a context-personality-cognitive state mapping knowledgebase (CKB) 170 by machine learning as performed by the machine learning process 150, such that later predictions on subsequent actions in certain event scenarios and cognitive states of users having certain personality in performing the predicted subsequent actions for generating the intelligent alarm 199.

The personality analyzer 130 of the intelligent alarm process 120 generates the user personality 121. In this specification, the term "personality" refers to a general tendency of emotional states and/or behaviors, and the term "cognitive state" refers to a momentary state of mind of an individual. Also, the term "event" refers to single or a group of occasions for which the intelligent alarm may be set, and the term "event scenario" refers to a typical progression of actions in the event, in which a series of correlated tasks are to happen in an orderly fashion. The term "context" refers to total circumstances of the event, wherein respective conditions are represented by each context attribute. In one embodiment of the present invention, the personality analyzer 130 may be implemented by use of external personality analysis service, by which personalities are determined based on psycholinguistic models by analyzing words used by the user 101. Details of personality analysis are furthered in block 210 of FIG. 2 and corresponding description.

The intelligent alarm process 120 predicts a subsequent action and a cognitive state of the user 101 during performing the predicted subsequent action based on the user data 103 and at least one context-personality-cognitive state (CPC) mapping from the CKB 170. The intelligent alarm process 120 generates the intelligent alarm 199 for the user 101 based on the predicted subsequent action, the corresponding cognitive state, and relevant CPC mapping and notifies the user 101 at various leading time configured based on the significance of the event, a role of the user 101 in the event, cognitive states and personality concerns, etc. For example, for the user 101 who has a personality "anxious" has an event "early morning flight" in a context "rainy", and "bad ground traffic", the intelligent alarm process 120 predicts the subsequent/required action to travel to the airport by leaving home earlier than in a good weather and/or regular ground traffic. Also, the intelligent alarm process 120 generates the intelligent alarm 199 that the user 101 should leave home an extra hour earlier than another user who is not ordinarily anxious, based on prediction that the user 101 would be in anxious/nervous cognitive state for travel to the airport.

Conventionally, the user 101 manually sets alarms for individual occasions and manages each alarm, on time/scheduling devices such as mobile phones, watches. Setting and managing separate alarms for each event may be cumbersome to maintain. Also, where circumstances of a same event may change and need distinctive amount of alarm schedule, the user 101 need to treat the alarms as for separate events. For example, if the user 101 sets a wake-up alarm for a work schedule that varies over the weekdays, and if the user 101 has an exercise class with a varying schedule for three (3) days during the weekdays, which also affects morning commute routes and time, the user 101 need to factor in many things to set the wake-up alarm for each weekday to coordinate with other schedules.

In contrast to conventional alarms, the intelligent alarm process 120 automatically sets the intelligent alarm 199 for an event based on the personality and the cognitive state of the user 101, and context/characteristics of an event for which the intelligent alarm 199 is generated. For example, in cases where the user 101 is in a nervous state, the intelligent alarm process 120 may be configured to set the intelligent alarm 199 earlier than in cases where the same user 101 is in a calm state, for a same type of event under the same circumstances. Also in cases where the user 101 has an anxious personality, the intelligent alarm process 120 may be configured to set the intelligent alarm 199 much earlier than in cases where the user 101 has a carefree personality, for a same type of event under the same circumstances. In addition, where an event is time-critical and/or of greater significance, the intelligent alarm process 120 may be configured to set the intelligent alarm 199 earlier than for an event that is more flexible and/or less significant. Further, the intelligent alarm process 120 may take other context information of the event into account such as current situation of the user in regard to the event schedule, availability of resources, circumstances/characteristics of the event, etc., in generating the intelligent alarm 199. The intelligent alarm service may be offered as a part of larger mobile communication service platforms, customer mobile devices, etc., to improve present solutions as well as to improve productivity by minimizing lost opportunities caused by preventable mistakes in keeping event schedules.

Figure 2:
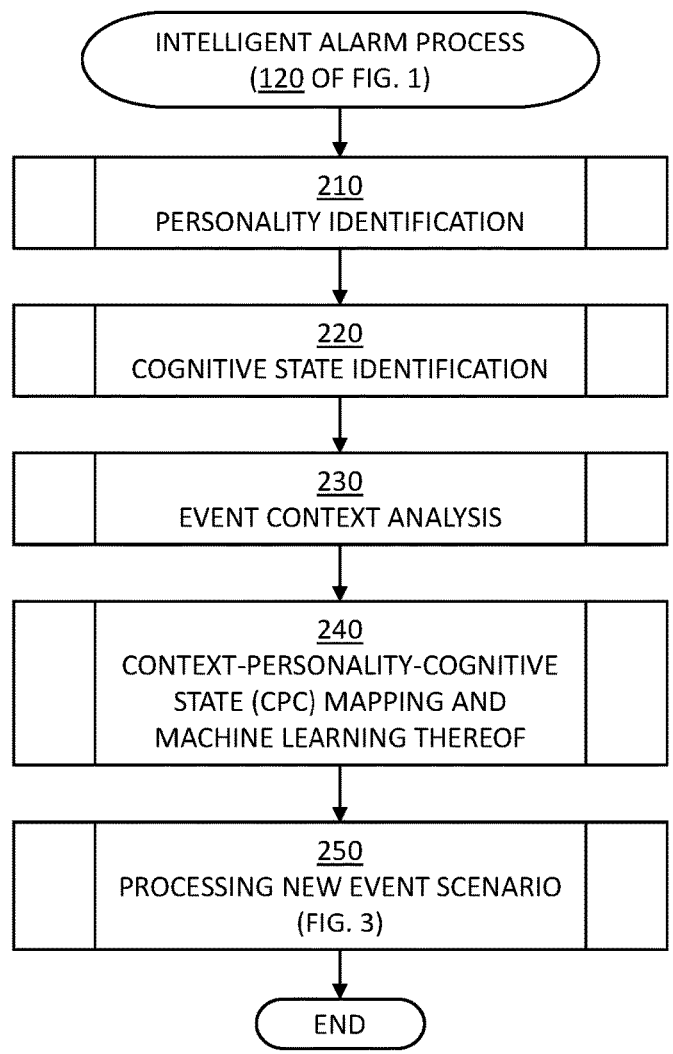
FIG. 2 depicts a flowchart performed by the intelligent alarm process, in accordance with one or more embodiments set forth herein.

FIG. 2 depicts a flowchart performed by the intelligent alarm process 120 of FIG. 1, in accordance with one or more embodiments set forth herein.

In block 210, the intelligent alarm process 120 gathers user data including personality data from the user device 110, responsive to the data collection agent 115 sending the user data 103 including the personality data. By analyzing the received personality data, the intelligent alarm process 120 identifies the personality of the user 101. In this specification, the personality of the user 101 dictates a general tendency of behaviors/reactions by the user 101 when the user 101 faces certain events. For example, by analyzing the tone of comments written by the user 101 reacting to various social media postings, the intelligent alarm process 120 may identify the user 101 as being generally neutral, agitated, etc. Then the intelligent alarm process 120 proceeds with block 220.

In certain embodiments of the present invention, the intelligent alarm process 120 may employ an external personality analysis service for personality analysis and determination.

In certain embodiments of the present invention, the data collection agent 115 running on the user device 110, a data collection software installed on various networking sites including a home network and social media networks, and combinations thereof, gathers user data 103 and sends the user data 103 to the intelligent alarm process 120 prior to block 210. The user data 103 collectively refers to all types of data utilized by the intelligent alarm process 120. The user data 103 may include event data, personality data, and cognitive state data. The personality data of the user data 103 may include a piece of writing authored by the user 101 in order to analyze the personality of the user 101. Examples of the personality data may include, but are not limited to, social media postings by the user 101, web blogs by the user 101, commentaries by the user 101 on news postings, etc. The personality of the user 101 may be stored in a user profile for the user 101 and retrieved for a specific event wherein the user profile has been established by a repeated use of the intelligent alarm service over time, without determining the personality of the user 101 for every event. In certain embodiments of the present invention, the intelligent alarm process 120 may operate without the personality of the user, by use of a predefined default, wherein the user profile has not been established and the external personality analysis service is not available. Examples of the user device 110 may include, but are not limited to, a wearable/mobile device of the user 101, a home network of the user 101, having various biometric sensors, microphones, cameras, and other similar sensors, for aforementioned respective monitoring.

In block 220, the intelligent alarm process 120 processes the cognitive state data of the user data 103, and identifies various cognitive states of the user. The cognitive state data of the user data 103 may include numerous physiological and/or behavioral data originating from the user 101, in order to determine a cognitive state of the user 101. Examples of the cognitive state data may include, but not limited to, biometric and physiological data of the user 101, such as a heart rate, a blood pressure, eye dilation, body temperature, and perspiration as acquired by body monitoring, voice stress level data as acquired by speech monitoring, body language and facial expression as acquired by video monitoring, etc. Then the intelligent alarm process 120 proceeds with block 230.

In block 230, the intelligent alarm process 120 identifies an event and analyzes context of the event based on the event data. The event data of the user data 103 may include various calendar events in which the user 101 partakes, and context details of each event, as represented by respective context attributes, such as date and time, location, weather, traffic, travel route and distance, a manner of transportation, actions/activities of the event, a type of the event, participants of the event, characteristics of the participants, the role of the user 101 in the event, etc. The intelligent alarm process 120 further identifies various cognitive states in which the user 101 may be, in association with the context of the event. Then the intelligent alarm process 120 proceeds with block 240.

For example, if there are three (3) participants for the event "Air travel" and the user is supposed to provide transportation to the airport, then the role of the user may be determined as critical for the event. Also, the significance of the event may be far greater for an event "International flight" than for a regular dental checkup "Dentist's appointment", which may be relatively easily rescheduled without consequences than the international flight. Accordingly, the cognitive state of the user may be more alert and/or nervous for such significant events, which translates into a longer leading time in notification of the intelligent alarm. Wherein a default leading time of notification for an ordinary significance is additional fifteen (15) minutes to travel time from the user location to the place of the event, the "International flight" may be configured for additional hour of leading time.

In block 240, the intelligent alarm process 120 builds context-personality-cognitive state (CPC) mappings by associating the various cognitive states, the context, and the personality of the user 101, as identified from blocks 210 through 230. The intelligent alarm process 120 subsequently processes the CPC mappings by machine learning such that the updated CPC mapping knowledgebase (CKB) 170 may be utilized to predict cognitive state of the users in future event contexts. Then the intelligent alarm process 120 proceeds with block 250.

In one embodiment of the present invention, examples of CPC mappings may be configured with context elements of weather, action, and group. For User A, whose personality is identified as being prone to worry and susceptible to stress, examples of CPC mappings, configured as a quintuple [context1—weather: context2—action: context3—company: personality: cognitive state], may be, [Sunny: Travel to airport: Group: Prone to worry: Calm—happy], [Sunny: Travel to airport: Alone: Prone to worry: Anxious], [Rainy: Travel to airport: Group: Prone to worry: Nervous], etc. With the same quintuple configuration of the CPC mappings, for User B, whose personality is identified as being confident and self-assured, examples of CPC mappings may be, [Sunny: Travel to airport: Alone: Confident: Calm], [Rainy: Travel to airport: Group: Confident: Calm], etc.

In block 250, the intelligent alarm process 120 processes a new event scenario from the latest updates in the user data 103, and generates the intelligent alarm 199 for an action in the new event for the user 101. An event scenario represents a series of actions in an event. For the example same as block 230, the action "Travel to airport" may be a part of an event "Air travel" that has a sequence of a first action "Ticketing", a second action "Packing", a third action "Travel to airport" as appearing in the previous examples of the CPC mappings, and a fourth action "Boarding".

Figure 3:
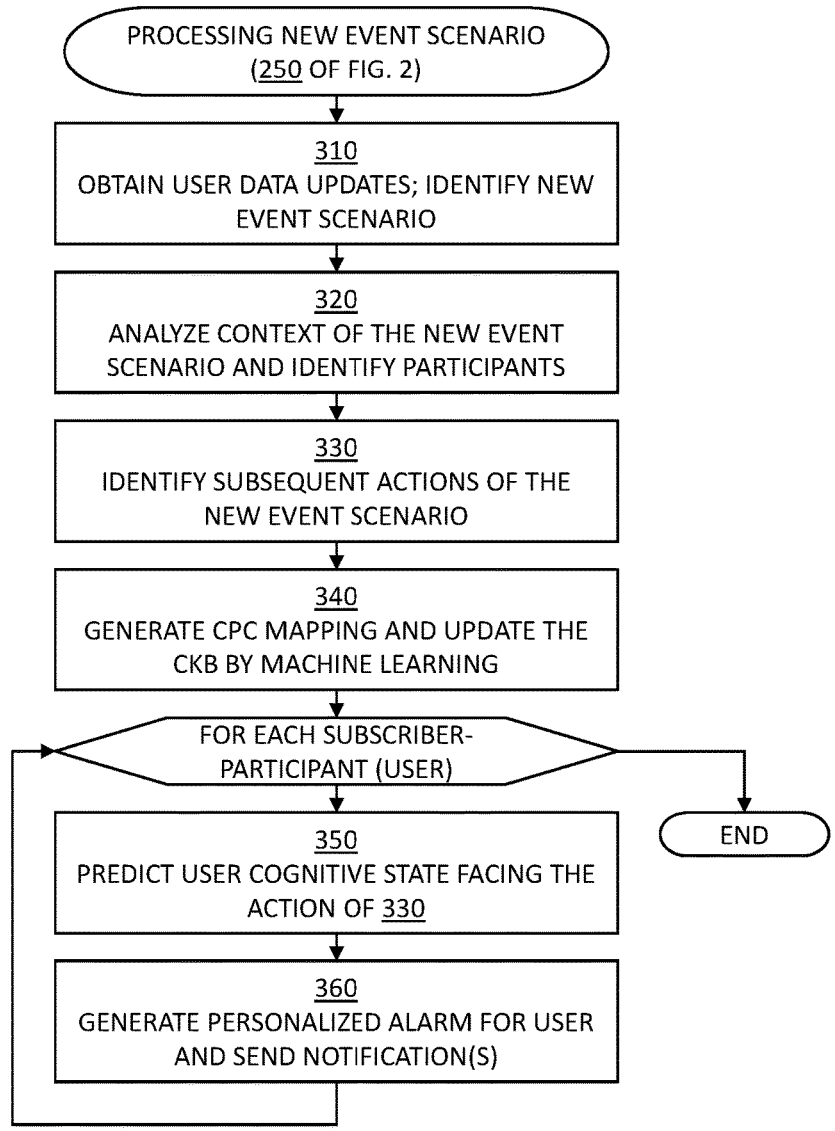
FIG. 3 depicts a detailed flowchart of new event scenario processing from the intelligent alarm process, in accordance with one or more embodiments set forth herein.

Blocks 210 and 240 collectively represent processes establishing the CKB 170 prior to a specific event, while block 250 describes how to handle the new event scenario, which are detailed in FIG. 3 and corresponding description. Then the intelligent alarm process 120 concludes processing the user data 103, obtained in blocks 210 and/or 250. The intelligent alarm process 120 may iterate block 250 for each new event scenario and updates the CKB 170 with new CPC mappings corresponding to the new actions in the new event scenarios.

FIG. 3 depicts a detailed flowchart of new event scenario processing as performed in block 250 of FIG. 2, in accordance with one or more embodiments set forth herein.

In block 310, the intelligent alarm process 120 obtains updates of the user data 101. Based on the updates of the user data, 103, the intelligent alarm process 120 identifies a new event scenario. In the exemplary event scenario from blocks 230 and 250, the actions "Packing" is subsequent to the action "Ticketing", the action "Travel to airport" is subsequent to the action "Packing", and the action "Boarding" is subsequent to the action "Travel to airport", as the event scenario is an ordered sequence of actions. In the same example, if the updated user data indicates that the user 101 does not make it to the boarding area in the airport by departure time, according to location data of the user at the departure time, the action "Boarding" would not be an action subsequent to "Travel to airport", and a new event scenario may be identified. Then the intelligent alarm process 120 proceeds with block 320.

As noted, the user data 101 updates include voice data, body language, social network postings, etc. Further, the user data 101 updates may be pluggable as generated by email appointments, calendar events, etc.

In block 320, the intelligent alarm process 120 analyzes context of the new event scenario identified in block 310, and identifies participants of the new event scenario. Then the intelligent alarm process 120 proceeds with block 330.

In certain embodiments of the present invention, the context of the new event scenario may include categories of the event based on criticality of the event, which may be measured in terms of consequences of the event and/or importance to be on schedule with the new event scenario, as noted in block 230 of FIG. 2.

In certain embodiments of the present invention, the intelligent alarm process 120 may factor in participants of the event who are not subscribers to the intelligent alarm service as context attributes, in block 320. Also, the intelligent alarm process 120 may analyze the context of the new events based on the respective roles of each participant in the new event scenario. For example, where the event is a car-pool trip, the intelligent alarm process 120 alerts a participant who drives a car in a more heightened level than other passenger-participants, because the event depends on timeliness of the driver-participant. All passenger-participants may be alerted in the same level as all other passengers, which is lower than the driver-participant, because an individual passenger-participant may not keep the schedule without endangering the event for all other participants. For another example, where the event is a party, the intelligent alarm process 120 alerts all guest participants with a same level, as each participant may independently act. The user data 101 updates may include a personality change of a user based on the context of the new event scenario.

In block 330, the intelligent alarm process 120 identifies various subsequent actions in the new event scenario. The intelligent alarm process 120 may identify the subsequent actions by use of machine learning based on interdependencies, causal relationships, and/or sequential progression of the actions in the new event scenario, as well as respective roles of individual participants in the new event scenario. Alternatively, the user 101 may specify a subsequent action in the new event scenario, when the intelligent alarm process 120 is configured for user input on the subsequent actions. Then the intelligent alarm process 120 proceeds with block 340.

In block 340, the intelligent alarm process 120 generates context-personality-cognitive state (CPC) mapping for the subsequent actions in the new event scenario as identified in block 330. The intelligent alarm process 120 subsequently updates the CPC mapping knowledgebase (CKB) 170 with the generated CPC mappings. Then the intelligent alarm process 120 proceeds with block 350.

The intelligent alarm process 120 performs blocks 350 and 360 for each participant of the new event scenario who is also a subscriber of the intelligent alarm services. For brevity, the subscriber-participant of blocks 350 and 360 is referred to as the user.

In block 350, the intelligent alarm process 120 predicts a cognitive state of the user at the time of action as identified from block 330, in the new event scenario. The intelligent alarm process 120 makes the prediction of the cognitive states based on the context and the personality in applicable CPC mappings from the updated CKB 170 from block 340. The applicable CPC mappings may have event contexts and user personalities similar to the subsequent action and the personality of the user 101. Then the intelligent alarm process 120 proceeds with block 360.

In block 360, the intelligent alarm process 120 generates a personalized alarm pursuant to the cognitive state of the user as predicted from block 350, and notifies the same to the user. Then the intelligent alarm process 120 concludes processing the user data updates received from block 310. In cases where dynamic reminders are requested based on a real time progression of the new event scenario, the intelligent alarm process 120 may reiterate blocks 310 through 360 in order to generate and to notify one (1) or more personalized alarm.

In certain embodiments of the present invention, the intelligent alarm process 120 automatically schedule a notification based on cognitive state and actions of other participants in the same group as predicted from block 350 by use of the CKB 170. When the intelligent alarm process 120 generates the personalized alarm for one user, the intelligent alarm process 120 may balance respective cognitive states of all users such that a laid-back user would get properly motivated to keep the schedule, and simultaneously, an anxious user in the same group would also get enough leading time not to get anxious. In certain embodiments of the present invention, the intelligent alarm process 120 may further notify the users with the respective cognitive states of other users in the same group such that the laid-back user may be informed that the anxious user gets nervous with a shorter leading time, or such that the anxious user may be informed that the laid-back user gets bored with a too much leading time, in order to facilitate the schedule for the group to be most acceptable for each user in the group.

Certain embodiments of the present invention may offer various technical computing advantages, including automated personal alarm notification based on predictions of elementary actions in an event and cognitive states of a user performing the elementary actions. Various data to assess personalities/cognitive states of users, contexts of the events are gathered and analyzed to predict and to map a context of the event, a personality of the user, and a present cognitive state of the user. Certain embodiments of the present invention improves the accuracy of the predictions on elementary actions of the events and the cognitive states of the users who perform the actions by use of machine learning. Certain embodiments of the present invention improves the productivity of individual users by automatically notifying the users on the events the users are meant to partake, by use of seamless data collection and prediction.

Figure 4:
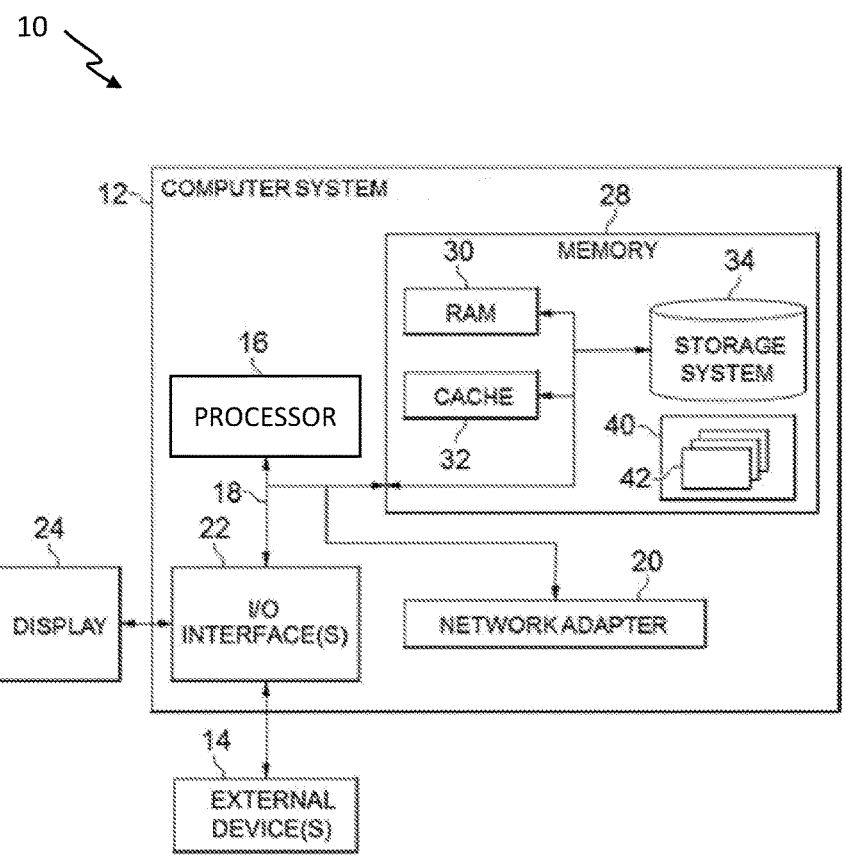
FIG. 4 depicts a cloud computing node according to an embodiment of the present invention.
Figure 5:
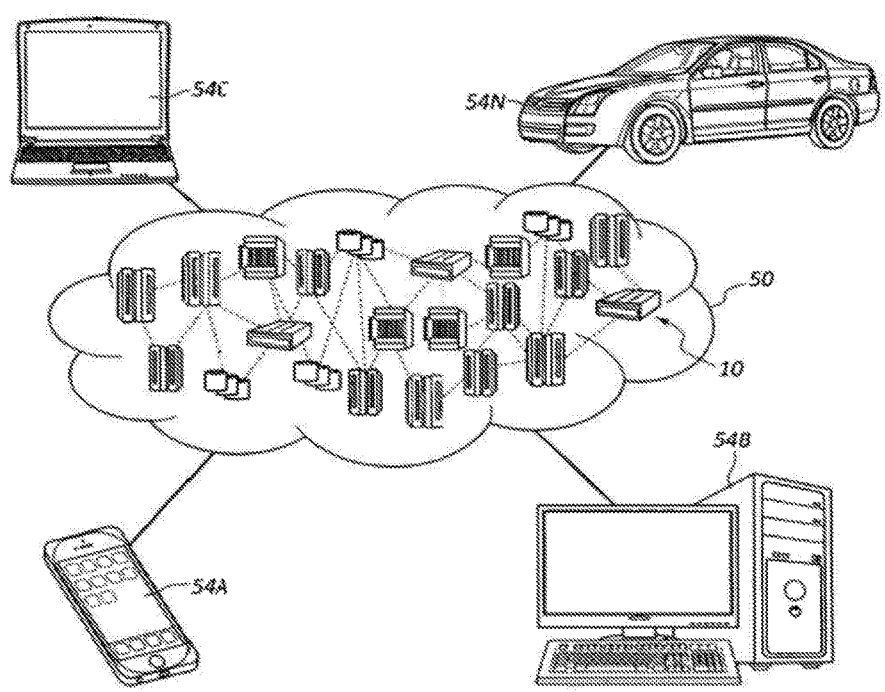
FIG. 5 depicts a cloud computing environment according to an embodiment of the present invention.
Figure 6:
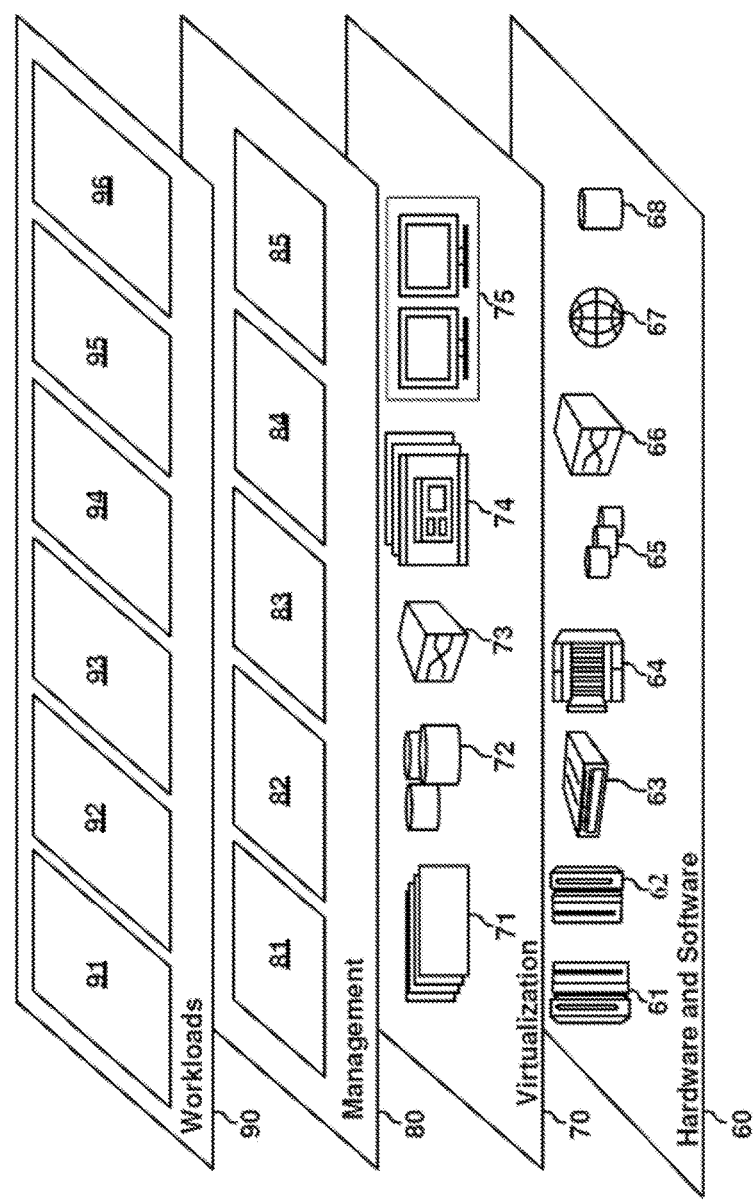
FIG. 6 depicts abstraction model layers according to an embodiment of the present invention.

FIGS. 4-6 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a computer system/cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 4, computer system 12 in cloud computing node 10 is shown in the form of a general-purpose computing device. The components of computer system 12 may include, but are not limited to, one or more processors 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. Each of the operating system, one or more application programs, other program processes, and program data or some combination thereof, may include an implementation of the intelligent alarm process 120 of FIG. 1. Program processes 42, as in the intelligent alarm process 120 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processors, external disk drive arrays, RAID systems, tape drives, and data archival storage systems, etc.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components for the intelligent alarm process 96, as described herein. The processing components 96 can be understood as one or more program 40 described in FIG. 4.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method for customizing an alarm for a user, comprising:
   collecting, by one or more processor, user data from the user;
   analyzing a context of an event from the user data, wherein the event comprises one or more actions;
   identifying subsequent actions of the event based on the context of the event and participants of the event;
   creating one or more context-personality-cognitive state (CPC) mapping;

adding the one or more CPC mapping to a knowledgebase by machine learning;
predicting a first cognitive state of the user while performing a first subsequent action amongst the subsequent actions of the event by use of the knowledgebase; and
generating the alarm for the first subsequent action based on the predicted first cognitive state of the user and notifying the generated alarm to the user.

2. The computer implemented method of claim 1, wherein the collecting is performed by use of one or more data collection agent sending the user data, wherein the user data may include event data, personality data, and cognitive state data, based on respective utility of the user data.

3. The computer implemented method of claim 1, the analyzing comprising:
identifying respective context attributes of the event from the user data including at least one calendar event and corresponding details, that may be selected from date and time of the event, location of the event, weather at a specific time, traffic at a certain time and location, a travel route and distance, a manner of transportation, one or more actions of the event, a type of the event, zero or more participants of the event, characteristics of the participants, the role of the user in the event, and combinations thereof.

4. The computer implemented method of claim 1, further comprising:
identifying a personality of the user based on analyzing the user data, wherein the user data utilized for the identifying the personality may include a piece of writing authored by the user such that the personality of the user is identified by use of natural language processing and personality analytics, selected from social media postings by the user, web blogs by the user, commentaries by the user on news postings, and all digital writings that is authored by the user.

5. The computer implemented method of claim 1, further comprising:
identifying a cognitive state of the user based on analyzing the user data, wherein the user data utilized for the identifying the cognitive state may include one or more physiological and/or behavioral data originating from the user, selected from the listing comprising body monitoring data, speech monitoring data, video monitoring data, and combinations thereof, wherein the body monitoring data may include a heart rate, a blood pressure, eye dilation, body temperature, and perspiration by the user, the speech monitoring data may include voice stress level data, the video monitoring data may include body language and facial expression.

6. The computer implemented method of claim 1, wherein the CPC mapping associates a context of the event, a personality of the user, and a cognitive state of the user such that the cognitive state may be determined based on the context of the event and the personality of the user of other CPC mappings having similar event contexts and personalities.

7. The computer implemented method of claim 1, the generating comprising:
setting the alarm earlier than a default configuration based on determining that the predicted first cognitive state of the user due to various context attributes of the event, and informing participants of the event of the predicted first cognitive state of the user such that all participants of the event may balance respective cognitive states with one another for the first subsequent action.

8. A computer program product comprising:
a computer readable storage medium readable by one or more processor and storing instructions for execution by the one or more processor for performing a method for customizing an alarm for a user, comprising:
collecting, by the one or more processor, user data from the user;
analyzing a context of an event from the user data, wherein the event comprises one or more actions;
identifying subsequent actions of the event based on the context of the event and participants of the event;
creating one or more context-personality-cognitive state (CPC) mapping;
adding the one or more CPC mapping to a knowledgebase by machine learning;
predicting a first cognitive state of the user while performing a first subsequent action amongst the subsequent actions of the event by use of the knowledgebase; and
generating the alarm for the first subsequent action based on the predicted first cognitive state of the user and notifying the generated alarm to the user.

9. The computer program product of claim 8, wherein the collecting is performed by use of one or more data collection agent sending the user data, wherein the user data may include event data, personality data, and cognitive state data, based on respective utility of the user data.

10. The computer program product of claim 8, the analyzing comprising:
identifying respective context attributes of the event from the user data including at least one calendar event and corresponding details, that may be selected from date and time of the event, location of the event, weather at a specific time, traffic at a certain time and location, a travel route and distance, a manner of transportation, one or more actions of the event, a type of the event, zero or more participants of the event, characteristics of the participants, the role of the user in the event, and combinations thereof.

11. The computer program product of claim 8, further comprising:
identifying a personality of the user based on analyzing the user data, wherein the user data utilized for the identifying the personality may include a piece of writing authored by the user such that the personality of the user is identified by use of natural language processing and personality analytics, selected from social media postings by the user, web blogs by the user, commentaries by the user on news postings, and all digital writings that is authored by the user.

12. The computer program product of claim 8, further comprising:
identifying a cognitive state of the user based on analyzing the user data, wherein the user data utilized for the identifying the cognitive state may include one or more physiological and/or behavioral data originating from the user, selected from the listing comprising body monitoring data, speech monitoring data, video monitoring data, and combinations thereof, wherein the body monitoring data may include a heart rate, a blood pressure, eye dilation, body temperature, and perspiration by the user, the speech monitoring data may include voice stress level data, the video monitoring data may include body language and facial expression.

13. The computer program product of claim 8, wherein the CPC mapping associates a context of the event, a personality of the user, and a cognitive state of the user such that the cognitive state may be determined based on the context of the event and the personality of the user of other CPC mappings having similar event contexts and personalities.

14. The computer program product of claim 8, the generating comprising:
setting the alarm earlier than a default configuration based on determining that the predicted first cognitive state of the user due to various context attributes of the event, and informing participants of the event of the predicted first cognitive state of the user such that all participants of the event may balance respective cognitive states with one another for the first subsequent action.

15. The computer program product of claim 8, the generating comprising:
setting the alarm earlier than a default configuration based on determining that the predicted first cognitive state of the user due to various context attributes of the event, and informing participants of the event of the predicted first cognitive state of the user such that all participants of the event may balance respective cognitive states with one another for the first subsequent action.

16. A system comprising:
a memory;
one or more processor in communication with memory; and
program instructions executable by the one or more processor via the memory to perform a method for customizing an alarm for a user, comprising:
collecting, by the one or more processor, user data from the user;
analyzing a context of an event from the user data, wherein the event comprises one or more actions;
identifying subsequent actions of the event based on the context of the event and participants of the event;
creating one or more context-personality-cognitive state (CPC) mapping;
adding the one or more CPC mapping to a knowledgebase by machine learning;
predicting a first cognitive state of the user while performing a first subsequent action amongst the subsequent actions of the event by use of the knowledgebase; and
generating the alarm for the first subsequent action based on the predicted first cognitive state of the user and notifying the generated alarm to the user,
wherein the collecting is performed by use of one or more data collection agent sending the user data, wherein the user data may include event data, personality data, and cognitive state data, based on respective utility of the user data.

17. The system of claim 16, the analyzing comprising:
identifying respective context attributes of the event from the user data including at least one calendar event and corresponding details, that may be selected from date and time of the event, location of the event, weather at a specific time, traffic at a certain time and location, a travel route and distance, a manner of transportation, one or more actions of the event, a type of the event, zero or more participants of the event, characteristics of the participants, the role of the user in the event, and combinations thereof.

18. The system of claim 16, further comprising:
identifying a personality of the user based on analyzing the user data, wherein the user data utilized for the identifying the personality may include a piece of writing authored by the user such that the personality of the user is identified by use of natural language processing and personality analytics, selected from social media postings by the user, web blogs by the user, commentaries by the user on news postings, and all digital writings that is authored by the user.

19. The system of claim 16, further comprising:
identifying a cognitive state of the user based on analyzing the user data, wherein the user data utilized for the identifying the cognitive state may include one or more physiological and/or behavioral data originating from the user, selected from the listing comprising body monitoring data, speech monitoring data, video monitoring data, and combinations thereof, wherein the body monitoring data may include a heart rate, a blood pressure, eye dilation, body temperature, and perspiration by the user, the speech monitoring data may include voice stress level data, the video monitoring data may include body language and facial expression.

20. The system of claim 16, wherein the CPC mapping associates a context of the event, a personality of the user, and a cognitive state of the user such that the cognitive state may be determined based on the context of the event and the personality of the user of other CPC mappings having similar event contexts and personalities.

\* \* \* \* \*